United States Patent
Duong-Van

[11] Patent Number: 6,063,083
[45] Date of Patent: May 16, 2000

[54] ELECTROSURGERY BLADE HAVING DISCRETE POINT DISCHARGE SAW-TOOTH EDGE

[76] Inventor: Minh Duong-Van, 810-18 Coleman Ave., Menlo Park, Calif. 94025

[21] Appl. No.: 09/083,789

[22] Filed: May 22, 1998

[51] Int. Cl.[7] ..................................... A61B 17/39
[52] U.S. Cl. ............................ 606/45; 607/101
[58] Field of Search ................. 606/45–52, 41, 606/39; 30/372, 514

[56] References Cited

U.S. PATENT DOCUMENTS

| | | | |
|---|---|---|---|
| 4,161,950 | 7/1979 | Doss et al. | |
| 4,589,411 | 5/1986 | Friedman | |
| 5,395,363 | 3/1995 | Billings et al. | 606/41 |
| 5,674,220 | 10/1997 | Fox et al. | 606/51 |
| 5,700,261 | 12/1997 | Brinkerhoff | 606/41 |
| 5,891,142 | 4/1999 | Eggers et al. | 606/51 |
| 5,902,301 | 5/1999 | Olig | 606/48 |
| 5,951,549 | 9/1999 | Richardson et al. | 606/45 |

OTHER PUBLICATIONS

J.D. Bronzino (Ed), *The Biomedical Engineering Handbook*, 1995, Chapter 83, W.W. von Malzahn and J.L. Eggleston, "Electrosurgical Devices", pp. 1292–1300.

*Primary Examiner*—Linda C. M. Dvorak
*Assistant Examiner*—Roy Gibson
*Attorney, Agent, or Firm*—Steven Mitchell

[57] ABSTRACT

An electrosurgery blade active electrode having a plurality of discrete electrical discharge points along a blade edge. A plurality of distinct points are provided for current discharge, facilitating controlled evenly distributed current through the tissue. The more stable discharge allows cutting with reduced current thus substantially reducing problems of the electrode sticking to the tissue and reducing damage to surrounding tissue. Furthermore, the cutting speed is increased and the smoke generated in the cutting process is decreased with use of the inventive blade. The electrosurgery blade of the invention may also include a plurality of grooves or channels on the side of the blade leading from the blade edge to the back of the blade away from the cutting edge to facilitate the escape of heated gasses from the area of the cut.

18 Claims, 1 Drawing Sheet

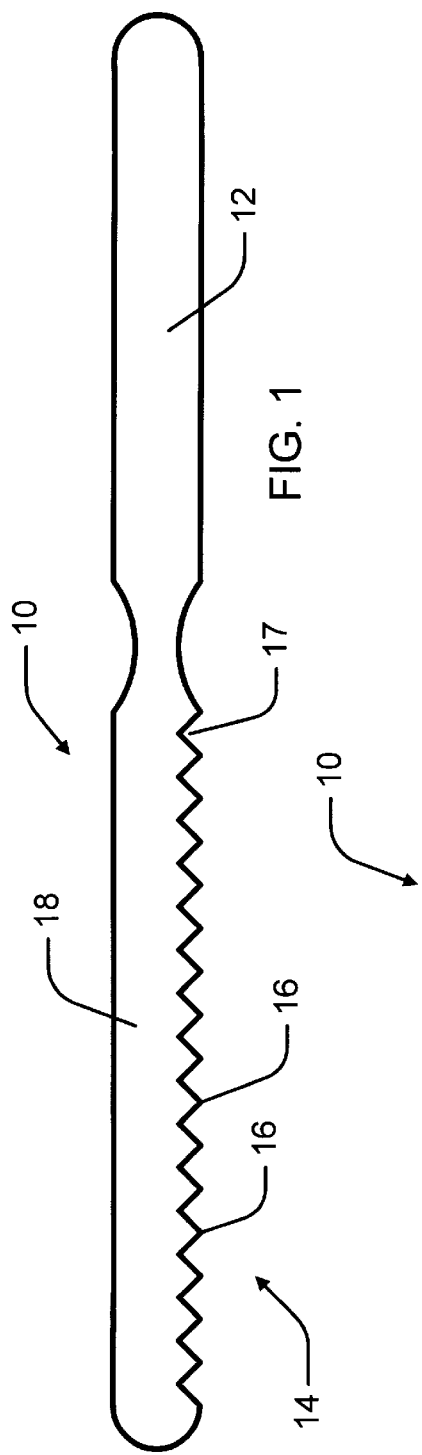
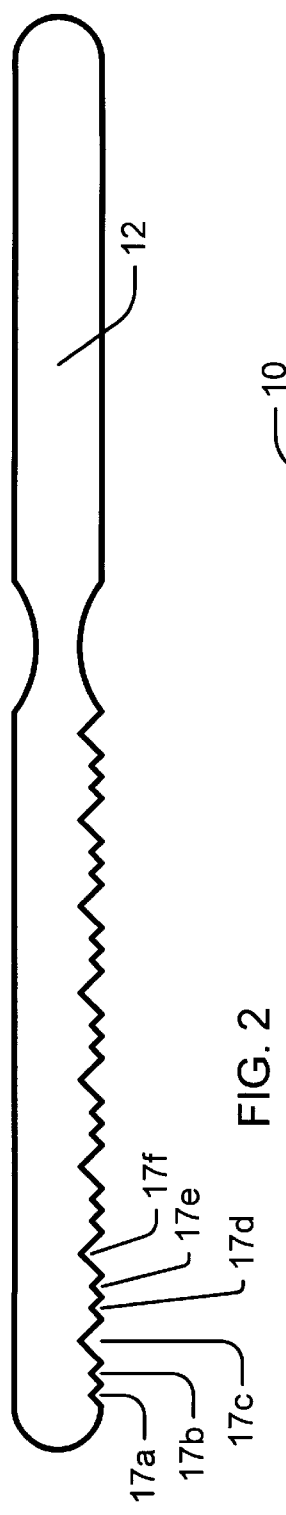
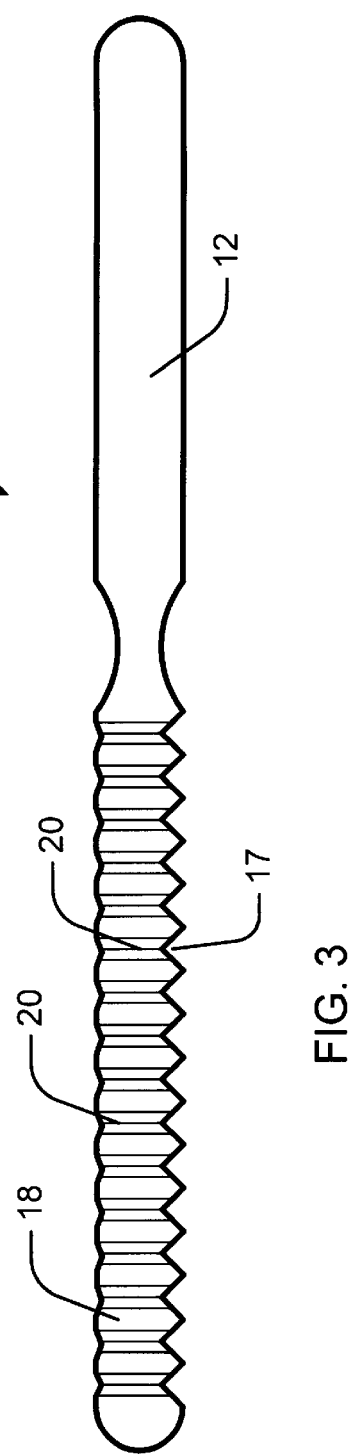
FIG. 1
FIG. 2
FIG. 3

ELECTROSURGERY BLADE HAVING DISCRETE POINT DISCHARGE SAW-TOOTH EDGE

FIELD OF THE INVENTION

The present invention relates generally to an apparatus for performing electrosurgery, and more particularly to an electrosurgical blade having a plurality of discrete points along the blade edge.

BACKGROUND OF THE INVENTION

In electrosurgery, a high-frequency electric current is passed through biologic tissues to achieve specific surgical effects such as cutting, coagulation, or desiccation. Electrosurgery allows cutting while at the same time controlling the amount of bleeding. Cutting is achieved primarily with a continuous sinusoidal waveform, whereas coagulation is achieved primarily with a series of sinusoidal wave packets. A surgeon using an electrosurgical unit (ESU) selects either one of these waveforms or a blend of them to suit the surgical needs.

An electrosurgical unit can be operated is two modes, the monopolar mode and the bipolar mode. The most noticeable difference between these two modes is the method in which the electric current enters and leaves the tissue. In the monopolar mode, the current flows from a small active electrode into the surgical site, spreads though the body, and returns to a large dispersive electrode on the skin. The high current density in the vicinity of the active electrode achieves tissue cutting or coagulation, whereas the low current density under the dispersive electrode causes no tissue damage. In the bipolar mode, the current flows only through the tissue held between two forceps electrodes. The monopolar mode is used for both cutting and coagulation. The bipolar mode is used primarily for coagulation.

The effects of electrosurgery are based on the rapid heating of tissue. When tissue is rapidly heated above 45° C., irreversible changes take place that inhibit normal cell function and lead to cell death. First, between 45° C. and 60° C., the proteins in the cell lose their quaternary configuration and solidify into a glutinous substance that resembles the white of a hard-boiled egg. This process, termed coagulation, is accompanied by tissue blanching. Further increasing the temperature up to 100° C. leads to tissue drying; that is the aqueous cell contents evaporate. This process is called desiccation. If the temperature is increased beyond 100° C., the solid contents of the tissue reduce to carbon, a process referred to as carbonization.

In the monopolar mode, the active electrode either touches the tissue directly or is held a few millimeters above the tissue. It is important to note that the blade edge does not cut the tissue with an electrosurgical blade. Rather, it is the electric current which does the cutting. When the electrode is held above the tissue, the electric current bridges the air gap by creating an electric discharge arc. A visible arc forms when the electric field strength exceeds 1 kV/mm in the gap. The temperature inside a discharge location is of an order of thousands of degrees Centigrade, causing the formation of a plasma, which evaporates the tissue being cut. If the plasma does not have a chance to evacuate quickly, the trapped plasma will evaporate a larger pocket of tissue, thus creating a the larger wound. One problem with conventional electrosurgery blades is that this arcing is unstable as the arcs initiate from various locations on the blade edge and surface. The arc will typically initiate from somewhere on the blade edge since the electric current will tend to flow through the sharpest location on the electrode. This instability requires greater current and thus more localized heating of the tissue. Thus, it would be an advancement in the art to provide an active electrode capable of discharging electric current with a substantially uniform distribution. It would also be desirable to reduce the size of the cutting wound caused by the electrosurgical blade.

A problem with the use of electrosurgery blades is that of undesirable current concentration due to contact between the active electrode and the tissue. This is exacerbated by the tendency of some bare metal electrodes to stick to tissue. When an electrode sticks to tissue, much or all of the electrical current discharged from the electrode may pass through the same portion of the patient's body. The resulting burns may substantially increase the patient's healing period. In addition, of course, tissue is damaged when a sticking electrode is pulled away from the tissue. This problem has been addressed in part in the prior art with the use of various "non-stick" coatings such as silicon, Teflon® and titanium nitride. It would be desirable to further reduce the problem of tissue sticking by reducing the heating of the electrode separate from or in addition to such coatings. It would thus be an advancement in the art to provide an active electrode for electrosurgery that required less current for cutting.

One of the more undesirable properties of electrosurgery is the smoke which is generated by cutting which interferes with the ability of the surgeon to view the cut. Various designs have been developed to blow or suction the smoke away from the region of the cut. It would be desirable to provide a blade which substantially reduces the amount of smoke generated in connection with cutting using an electrosurgical blade.

SUMMARY OF THE INVENTION

The apparatus of the present invention provides an electrosurgery blade active electrode having a plurality of discrete electrical discharge points along a knife edge. This plurality of discrete points may be provided, for instance, by stamping or filing a serrated or "saw-blade" edge on the active electrode. The spacing of the discharge points along the blade may be a regular pattern or an irregular pattern such as a fractal or multifractal spacing. This provides a plurality of distinct points for current discharge, facilitating controlled evenly distributed current through the tissue. The more stable discharge allows cutting with reduced current thus facilitating reduced problems with the electrode sticking to the tissue and reduces damage to surrounding tissue during cutting.

The electrosurgery blade of the invention may also include a plurality of plasma evacuation groves or channels on the sides of the blade leading from the troughs on the blade edge to the back of the blade away from the cutting edge to facilitate the escape of heated gasses from the area of the cut.

The blades of the present invention may be used with a monopolar electrosurgical generator connected electrically to a dispersive return electrode which is fixedly attached to a patient during treatment. Such dispersive electrodes are conventionally orders of magnitude larger than the active electrode employed.

Alternatively, a bipolar embodiment of the present invention may be used. In such a bipolar embodiment, the return electrode is approximately the same size as the active electrode, and is fixed in position relative to the active electrode, not relative to the patient.

In view of the foregoing, it is a primary object of the present invention to facilitate improved cutting performance of an electrosurgery blade by providing an active electrode blade with a blade edge having a plurality of discrete electrical discharge points capable of applying current to tissue.

It is another object of the present invention to provide an active electrode that does not stick easily to tissue.

It is still another object of the present invention to provide an electrosurgical blade which results in a reduction in the size of the cutting wound.

BRIEF DESCRIPTION OF THE DRAWINGS

The various features and advantages of the present invention may be more readily understood with reference to the following detailed description taken in conjunction with the accompanying drawings in which:

FIG. 1 is a side view of one preferred embodiment of a monopolar electrosurgery blade having a regular saw-tooth edge;

FIG. 2 is a side view of an electrosurgery blade of the invention having a fractal configuration of discharge points; and FIG. 3 is a side view of an alternative embodiment of the invention having plasma evacuation channels.

DETAILED DESCRIPTION OF THE INVENTION

Reference is now made to the figures wherein like parts are referred to by like numerals throughout. FIG. 1 illustrates an electrosurgical blade 10 including a shaft 12 which can be inserted into an insulated handle (not shown) frequently referred to as a pencil. Such a handle or pencil is illustrated in U.S. Pat. Nos. 4,589,411 and 5,395,363, which patents are incorporated herein by reference. The pencil will conventionally include in its handle one or more switches to control the electrosurgical waveform, primarily to switch between cutting and coagulation. The blade has an edge 14 which includes a plurality of discrete discharge points or peaks 16 from which discharge arcs can jump to the tissue when cutting. The peaks 16 alternate with troughs 17. It has been discovered that a large number of discharge points such as about 20 provides the best results. The depth of the troughs 17 on the blade edge preferably extends down between about 0.25 mm and 1.0 mm from the peaks 16 on the blade edge with about 0.5 mm preferred. The spacing between adjacent peaks (and adjacent troughs) is correspondingly between about 0.25 and 1.0 mm with 0.5 mm preferred. In the embodiment shown in FIG. 1, the sides of the peaks have equal angles of about 45 degrees. These angles may be different and may be unequal such that, for example, the peaks point forward or backward along the blade edge.

An electrosurgical generator (not shown) produces the high frequency current that is transmitted through the blade 10 and the patient's body and to the return dispersive electrode (not shown).

FIG. 2 is a side view of a blade of an alternative embodiment of the invention with the discharge points having an irregular or fractal configuration. It is believed that a fractal configuration for the discharge points improves stability of the electrical discharge improving the cutting speed and reducing the generation of smoke. For the example shown in FIG. 2, the configuration exhibits a spacing and height of the peaks of 1:1:2:1:1:2 etc. Thus, moving from the tip of the blade, the first two troughs, 17a and 17b, have the same depth and the third trough 17c has a depth twice that of the first two. The next tow troughs 17d and 17e have the same depth as the first two troughs and the sixth trough 17f has the same depth as the third trough 17c. The pattern is continued along the blade.

Other examples of fractal configurations for the peaks are 1:2:1:4:1:2:1:4 etc. and 1:2:1:3:1:2:1:3 etc.

Alternatively, a multifractal configuration for the spacing and height of the peaks is possible. A multifractal configuration is a mixed set of fractals. An example of such a configuration is 1:1:1:2:1:2:1:1:1:3:1:3:1:1:1:2:1:2 etc.

FIG. 3 illustrates another alternative embodiment of the invention wherein the flat 18 of the blade 10 includes a plurality of plasma evacuation channels 20 leading from the troughs 17 on the blade edge to the back of the blade. This facilitates the escape of heated gasses from the area of the cut.

Those portions of the blade 10 which will contact tissue may be constructed to inhibit sticking. Sticking may be inhibited by constructing the blade of an appropriate metal, such as soft steel, stainless steel, titanium, or a suitable alloy. Sticking may also be inhibited by covering a portion of the exterior surface of the blade 10 with a nonstick coating such as polytetrafluoroethylene, which is sold commercially under the trademark TEFLON®.

Each of FIGS. 1–3 depicts a flat blade electrode 10, but cylinders, cones, or other shapes having a line of discrete discharge points may also be fruitfully employed in embodying the present invention.

It should be appreciated that the apparatus of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. An electrosurgical cutting tool for use with an electrosurgical generator comprising:

a monopolar active electrode for coupling to said electrosurgical generator, said blade having a longitudinal extent and an edge; and having a plurality of discrete radio frequency electrically conductive discharge points along said edge.

2. The tool of claim 1 wherein said blade includes a flattened portion and a plurality of channels in said flattened portion extending transverse to said longitudinal extent from said edge.

3. The tool of claim 1 wherein said plurality of discharge points have a regular spacing and height.

4. The tool of claim 1 wherein said plurality of discharge points have an irregular spacing and height.

5. The tool of claim 4 wherein said spacing and height of said discharge points has a fractal configuration.

6. The tool of claim 4 wherein said spacing and height of said discharge points has a multifractal configuration.

7. The tool of claim 1 wherein at least a portion of said blade includes a non-stick coating.

8. The tool of claim 1 wherein said conductive discharge points have a triangular shape.

9. A monopolar electrosurgical blade comprising:

a single longitudinal electrically conductive portion; and a plurality of discrete points distributed along said conductive portion.

10. The blade of claim 9 wherein said longitudinal electrically conductive portion includes a flattened portion and a plurality of channels in said flattened portion extending transverse to said longitudinal portion.

11. The blade of claim 9 wherein said plurality of discharge points have a regular spacing and height.

12. The blade of claim 9 wherein said plurality of discharge points have an irregular spacing and height.

13. The tool of claim 12 wherein said spacing and height of said discharge points has a fractal configuration.

14. The blade of claim 12 wherein said spacing and height of said discharge points has a multifractal configuration.

15. The blade of claim 9 wherein at least a portion of said blade includes a non-stick coating.

16. The blade of claim 9 wherein said conductive discharge points have a triangular shape.

17. A monopolar electrosurgery blade for use in an electrosurgery system including an electrosurgical generator and a large surface area dispersive return electrode coupled to said generator and for placement in contact with a patient's skin, said monopolar electrosurgery blade comprising:

a blade having a longitudinal extent and an edge; and said blade having a plurality of discrete radio frequency electrically conductive discharge points along said edge;

whereby cutting is achieved by electrical discharge from said discharge points on said blade to a patient's tissue.

18. The blade of claim 17 wherein said conductive discharge points have a triangular shape.

* * * * *